United States Patent [19]

Paul

[11] 4,206,230
[45] Jun. 3, 1980

[54] PHENYL CYCLOPROPYL KETONE INSECTICIDES

[75] Inventor: Jill H. Paul, Edgewater, N.J.

[73] Assignee: Mobil Oil Corporation, New York, N.Y.

[21] Appl. No.: 959,821

[22] Filed: Nov. 13, 1978

[51] Int. Cl.$^2$ .................... A01N 9/20; A01N 9/24; C07C 49/76; C07C 121/76
[52] U.S. Cl. .................... 424/304; 260/347.8; 260/465 F; 260/465 G; 260/465 R; 424/285; 424/331; 568/329; 568/64; 568/327; 568/331
[58] Field of Search .......... 260/465 F, 590 C, 590 D, 260/465 G; 424/331, 304

[56] References Cited

U.S. PATENT DOCUMENTS

| | | | |
|---|---|---|---|
| 3,878,200 | 4/1975 | Diana et al. | 260/590 D |
| 4,005,103 | 9/1974 | Teulon | 260/590 C |
| 4,024,163 | 5/1977 | Elliott et al. | 260/465 D X |

OTHER PUBLICATIONS

Berteau et al., Science, vol. 161, pp. 1151–1153 (1968).

*Primary Examiner*—Dolph H. Torrence
*Attorney, Agent, or Firm*—Charles A. Huggett; James F. Powers; Hastings S. Trigg

[57] ABSTRACT

There are provided insecticidal ketones having the general structure

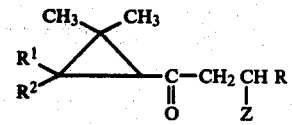

insecticidal compositions containing the ketones and a carrier, and the method of controlling insects with the ketones.

12 Claims, No Drawings

PHENYL CYCLOPROPYL KETONE INSECTICIDES

BACKGROUND OF THE INVENTION

1. Field of the Invention

This invention is concerned with certain ketones that have insecticidal activity.

2. Description of the Prior Art

The ketone insecticides of this invention have a similarity in structure to synthetic pyrethroid esters, such as permethrin, phenothrin, and resmethrin. Certain ketones have been reported to have some measure of insecticidal activity in Science 161, 1151–1153 (1968) and J. Agr. Food Chem. 17, 931–938 (1969). In these ketones, the R substituent is a substituted cyclopentenyl or furyl group. Such substituents are not contemplated in the compounds of this invention. Insofar as is now known, the ketones described herein have not been proposed.

SUMMARY OF THE INVENTION

This invention provides compounds having the formula

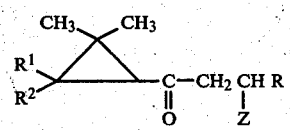

wherein $R^1$ and $R^2$ are methyl or $R^1$ is hydrogen and $R^2$ is diahalovinyl; Z is hydrogen or cyano; and R is

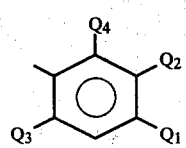

wherein $Q_2$ is phenyl, benzyl, phenoxy, propargyl, thiophenoxy, furfuryl, halogen, alkyl, hydrogen, oxothiophenyl or trifluoromethyl; $Q_1$ is hydrogen, chlorine, or trifluoromethyl; or $Q_1$ and $Q_2$ together can be cyclopentyl or cyclohexyl; $Q_3$ is hydrogen, methyl or chlorine; and $Q_4$ is hydrogen or methyl.

DESCRIPTION OF SPECIFIC EMBODIMENTS

In general, the insecticidal ketones of this invention are prepared:

General Scheme for Synthesis of Insecticidal Ketones

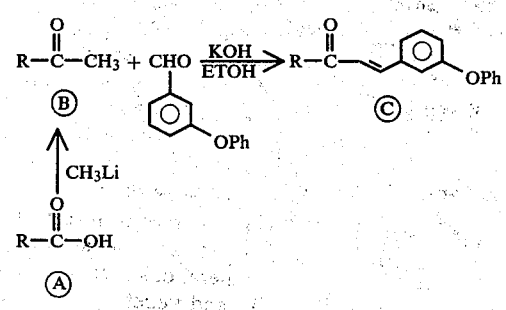

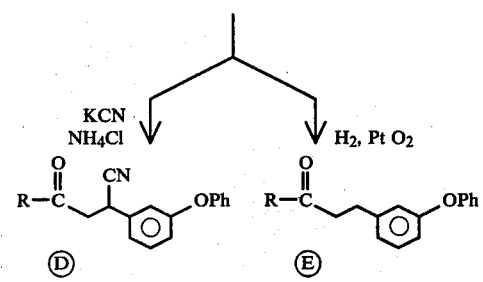

The preparation of starting carboxylic acid (A) is described in U.S. Pat. No. 4,024,163, when R is 3-dihalovinyl-2,2-dimethyl cyclopropyl. When R is 2, 2, 3, 3-tetramethylcyclopropyl, the carboxylic acid is prepared by an adaptation of a procedure in Pest. Sci., 5, 791–799 (1974), using 2,3-dimethyl-2-butene and ethyl diazoacetate followed by basic hydrolysis.

General Procedure for Methyl Ketones ((B))

To a solution of 0.047 mole of the appropriate carboxylic acid in 300 ml. of dry ether, is added dropwise 0.142 mole of $CH_3Li$, while maintaining the reaction temperature at 0° C. by means of an ice-salt bath. The reaction mixture is allowed to warm to R.T. and stirred overnight. The whole is poured into 80 ml. of conc. HCl over 800 ml. of ice. The layers are separated and the aqueous layer is extracted 2X with ether. The combined organic extracts are washed 1X with 10% $Na_2CO_3$, 1X with $H_2O$, dried over $MgSO_4$, and concentrated under reduced pressure to yield 0.038 mole of product.

IR $(Cm^{-1})$ 1709 (s).

General Procedure for α, β- Unsaturated Ketone ((C))

A mixture of 0.0095 mole of methyl ketone, 0.0136 mole of m-phenoxy benzaldehyde or other substituted benzaldehyde and 0.0025 mole of KOH in 70 ml. of EtOH is heated to 60° C., by means of a temperature control device for 16 hrs. Upon cooling, the whole is poured into 200 ml. of $H_2O$. The resulting oil is extracted into ether (2X). The ether extracts are washed with $H_2O$ and concentrated under reduced pressure. The residue is stirred with saturated $NaHSO_3$ for 1 hr. to remove the excess aldehyde. The bisulfite addition product is filtered off after dilution with ether. The ether layer of the filtrate is dried over $MgSO_4$ and concentrated under reduced pressure to yield 0.0064 mole of product.

Ir $(cm^{-1})$ 1695(s), 1666(s), 980(br,s).

General Procedure for β-Cyano Ketones ((D))

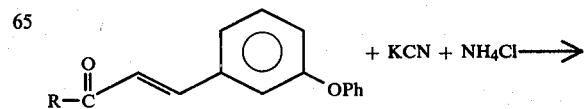

-continued

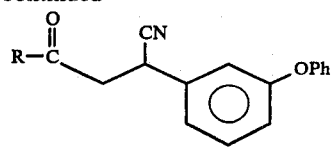

To a solution of 0.03 mole of the α, β unsaturated ketone dissolved in 120 ml. of DMF is added 0.06 m. of KCN in 25 ml. of H₂O, causing a slight exotherm. To this mixture is added 0.045 mole of ammonium chloride. The reaction mixture is heated to 98° C. for 5 hrs. The whole is poured into H₂O and the resulting oil taken up in ether. The ether extract is washed 3X with H₂O, dried, and concentrated under reduced pressure to yield 0.028 mole of product.

IR (cm$^{-1}$) 2272(s), 1724 (brs).

General Procedure for M-phenoxy Benzyl Ketones ((E))

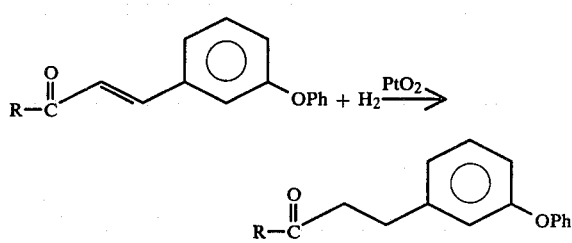

A solution of 0.03 mole of the α, β unsaturated ketone dissolved in 100 ml. of EtOAc and 100 mg. of PtO₂ is placed in a dry Parr Shaker hydrogenation bottle. H₂ is introduced overnight. The catalyst is filtered and washed with EtOAc. The filtrate is concentrated under reduced pressure to yield 0.03 mole of product.

IR (cm$^{-1}$) 1709(s).

Non-limiting examples of the ketones of this invention are:

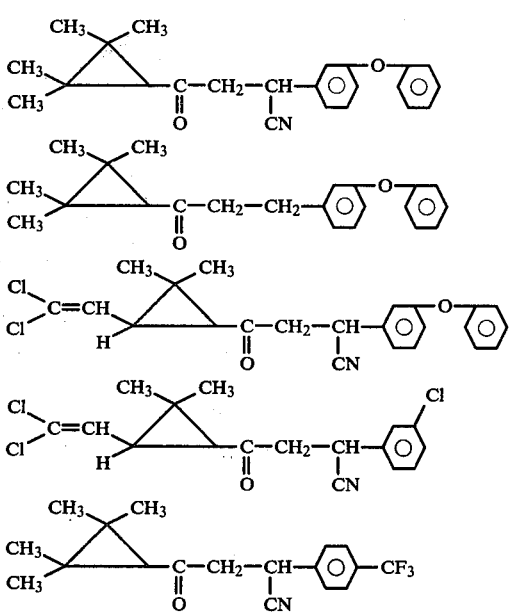

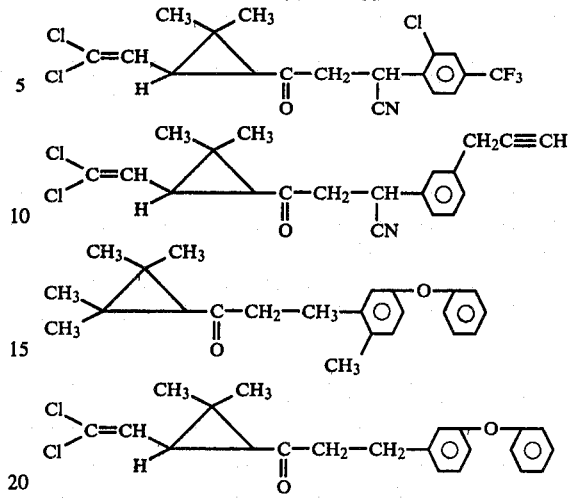

The following examples demonstrate compounds of this invention prepared using the general procedures described hereinbefore.

EXAMPLE 1

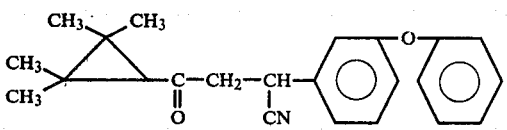

EXAMPLE 2

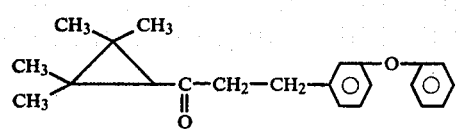

EXAMPLE 3

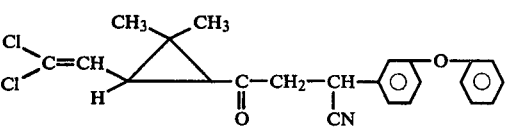

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophylite, fullers earth, gypsum, flours derived from cotton seeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying, dusting etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g. attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g. with kerosene. Thus, it is within the contemplation of this invention to provide pesticidal compositions containing up to about 80 percent, by weight of the composition, of a pesticidal compound of this invention. Accordingly, depending upon whether it is ready for application or it is in concentrated form, the contemplated insecticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24–75 hours. Compounds which product 90% mortality are reevaluated at lower concentrations in secondary tests. Mode of action may be by stomach poison, contact or vapor.

Stomach Poison - Foliar Dip Test

Primary Screen

Southern Armyworm (Larva)
Mexican Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm.

All test results are recorded as percent mortality. In the tabulation of data, the insect species are abbreviated as follows: Housefly (HF), Mexican Bean Beetle (MB) and Southern Armyworm (SA).

The compounds of Examples 1, 2, and 3 were subjected to the aforedescribed insecticide tests. Test concentrations and results are set forth in the Table.

TABLE

| Compound | Rate (PPM) | HF | SA | MB |
|---|---|---|---|---|
| Example 1 | 500 | 70 | 100 | 100 |
|  | 100 |  | 0 | 95 |
|  | 10 |  |  | 80 |
|  | 1 |  |  |  |
|  | 0.1 |  |  |  |
| Example 2 | 500 | 20 | 0 | 90 |
|  | 100 |  |  | 70 |
|  | 10 |  |  | 50 |
|  | 1 |  |  |  |
| Example 3 | 500 | 100 | 100 | 100 |
|  | 100 | 90 | 95 | 100 |
|  | 10 | 0 | 0 | 30 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Compounds having the formula:

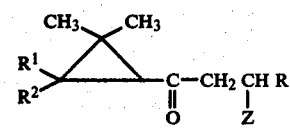

wherein $R_1$ and $R_2$ are methyl or $R_1$ is hydrogen and $R_2$ is dihalovinyl; Z is hydrogen or cyano; and R is

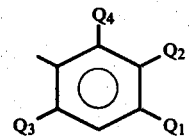

wherein $Q_2$ is phenyl, phenoxy, benzyl, propargyl, thiophenoxy, furfuryl, halogen, alkyl, hydrogen, oxothiophenyl, or trifluoromethyl; $Q_1$ is hydrogen, chlorine, or trifluoromethyl; or $Q_1$ and $Q_2$ together can be cyclopentyl or cyclohexyl; $Q_3$ is hydrogen, methyl or chlorine; and $Q_4$ is hydrogen or methyl.

2. A compound of claim 1 having the formula:

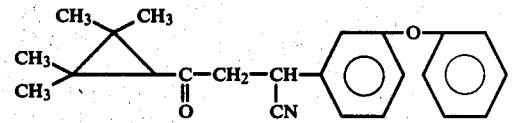

3. A compound of claim 1 having the formula:

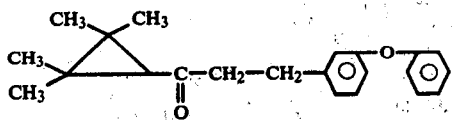

4. A compound of claim 1 having the formula:

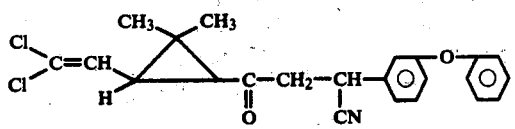

5. The method of combatting insects that comprises contacting them with an insecticidally effective amount of a compound of claim 1.

6. The method for combatting insects that comprises contacting them with an insecticidally effective amount of a compound of claim 2.

7. The method for combatting insects that comprises contacting them with an insecticidally effective amount of a compound of claim 3.

8. The method for combatting insects that comprises contacting them with an insecticidally effective amount of a compound of claim 4.

9. An insecticidal composition comprising a carrier and an insecticidally effective amount of a compound of claim 1.

10. An insecticidal composition comprising a carrier and an insecticidally effective amount of a compound of claim 2.

11. An insecticidal composition comprising a carrier and an insecticidally effective amount of a compound of claim 3.

12. An insecticidal composition comprising a carrier and an insecticidally effective amount of a compound of claim 4.

* * * * *

UNITED STATES PATENT AND TRADEMARK OFFICE
CERTIFICATE OF CORRECTION

PATENT NO. : 4,206,230
DATED : June 3, 1980
INVENTOR(S) : Jill H. Paul

It is certified that error appears in the above-identified patent and that said Letters Patent are hereby corrected as shown below:

Column 4, third diagram from the top, should read:

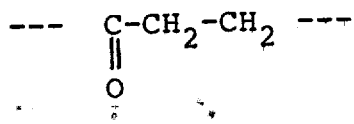

Column 6, line 44, "$R_1$" should read ---$R^1$---.

*Signed and Sealed this*

*Thirtieth* Day of *September 1980*

[SEAL]

*Attest:*

SIDNEY A. DIAMOND

*Attesting Officer* — Commissioner of Patents and Trademark